(12) United States Patent
Fakhrizadeh

(10) Patent No.: US 11,730,656 B2
(45) Date of Patent: Aug. 22, 2023

(54) APPARATUS FOR TREATING LOWER LIMB CONTRACTURES

(71) Applicant: Mohammad Fakhrizadeh, Saveh (IR)

(72) Inventor: Mohammad Fakhrizadeh, Saveh (IR)

( * ) Notice: Subject to any disclaimer, the term of this patent is extended or adjusted under 35 U.S.C. 154(b) by 987 days.

(21) Appl. No.: 16/556,208

(22) Filed: Aug. 29, 2019

(65) Prior Publication Data

US 2020/0078252 A1 Mar. 12, 2020

(51) Int. Cl.
*A61F 5/00* (2006.01)
*A61H 1/02* (2006.01)
*A61F 5/042* (2006.01)
*A61F 5/01* (2006.01)

(52) U.S. Cl.
CPC ......... *A61H 1/0266* (2013.01); *A61F 5/0127* (2013.01); *A61F 5/042* (2013.01); *A61F 2005/0153* (2013.01); *A61H 2201/0119* (2013.01); *A61H 2205/106* (2013.01); *A61H 2205/12* (2013.01)

(58) Field of Classification Search
CPC .................................................... A61F 5/0193
USPC .......................................................... 602/24
See application file for complete search history.

(56) References Cited

U.S. PATENT DOCUMENTS

| | | | | |
|---|---|---|---|---|
| 4,543,948 A | * | 10/1985 | Phillips | A61F 5/0104 602/23 |
| 5,401,235 A | * | 3/1995 | Devens | A61F 5/0193 602/23 |
| 8,118,764 B2 | * | 2/2012 | Christenhusz | A61F 5/0193 128/870 |
| 2007/0016122 A1 | * | 1/2007 | Bowman | A61F 5/0193 128/882 |
| 2011/0028876 A1 | * | 2/2011 | Mitchell | A61F 5/0127 602/29 |

* cited by examiner

*Primary Examiner* — Kim M Lewis

(57) ABSTRACT

An apparatus for treating lower limb contractures is disclosed. The apparatus comprises a pair of multi-sectional soles, which are movably affixed to a connector via a pair of arms using fasteners. The pair of soles are configured to support the user's feet. Each sole comprises four flat-solid plates, which are pivotally connected via hinges/fasteners. The four flat-solid plates are configured to cover, support, and align the user's feet. The apparatus further comprises a pair of ankle supports, securely and adjustably affixed to each sole, configured to support the user's ankle and lower leg. The plurality of straps is configured to secure the sole to the user's feet and lower leg while lifting and lowering the feet using additional straps that are coupled to one or more loops of the four-flat solid plates of the soles, thereby treating the limb contractures by facilitating the opportunity for the repetitive movement of every single joint and muscle in the lower limb of a the user.

13 Claims, 9 Drawing Sheets

APPARATUS FOR TREATING LOWER LIMB CONTRACTURES

BACKGROUND OF THE INVENTION

Limb contractures are a common impairment in neuromuscular diseases. Many people and children are suffering from limb contractures. Contracture in the lower limb is one of the adverse consequences of immobility. This is due to the shortening of the muscles and results in the deformation of the affected limb. In addition, there are 63 bones, including the hip bones, in the lower limb of a person. Ten of these bones are in the upper and lower leg, 14 bones are in the ankle, and 38 bones in the foot. There is cartilage between two adjacent bones and each bone is connected to and move in respect to the adjacent bones via several tendons and muscles. Immobility has adverse effects on the texture and the functionality of these body parts such as bone depletion, the fusing of adjacent bones, etc.

Currently, numerous devices such as an ankle-foot orthosis, splints, and braces and supports have been designed and used for the leg, hip, knee, ankle, and foot that can be used for a range of needs from stability to immobilization. An orthosis is a medical device that aims to support and align the ankle and foot by suppressing spastic and overpowering ankle and foot muscles, assisting weak and paralyzed muscles of the ankle and foot, and preventing or correcting ankle and foot deformities. In addition, bracing a limb by means of braces and supports in a stationary position for a long period time causes other problems such as body fluid stagnation, deep vein thrombosis, and stiffness of joints and tendons. The use of the existing splints is usually accompanied by pain, and the patient most likely would stop using them since they see no results even after long term use. Also, many types of splints are available in the market but still contractures prevail. Thus, there is a need for a device which indeed can prevent and treat limb contractures through facilitating opportunity for repetitive movement of every single joint and muscles in the lower limb, more particular in the feet, of a moving impaired person.

However, the conventional devices are expensive, inefficient, difficult to use, and uncomfortable for the user. For example, conventional devices, such as orthosis, fail to provide comfort and flexibility for the user while using and are not cost-effective. Further, the conventional devices do not positively influence the effect the wellbeing of the limb contractures. Thus, there is a need for new approaches to confront this problem.

Therefore, there is a clear and present need for an apparatus for effectively preventing or treating lower limb contractures. Further, there is also a need for an apparatus for providing comfort while using, which is economical to manufacture, durable, safe, inexpensive, and easy to use for the user.

SUMMARY OF THE INVENTION

The present invention generally relates to an ankle-foot moving apparatus and more particularly relates to an apparatus for treating or preventing lower limb contractures by facilitating the opportunity for the repetitive movement of every single joint and muscle in the lower limb of a moving impaired individual.

In one embodiment, the apparatus comprises a right shoe with a right sole and a left shoe with a left sole. In one embodiment, the right sole and the left sole of the right shoe and the left shoe of the apparatus are configured to support a bottom of the feet of a user. In one embodiment, the right sole and the left sole are movably affixed to a connector via a pair of arms or a right arm and a left arm, respectively, using one or more fasteners. In one embodiment, the right sole and the left sole of the apparatus comprise at least four solid-plates, which are securely and pivotally connected via hinges and fasteners. The four flat-solid plates are configured to cover, support, and align a tarsus portion, a metatarsal portion, a phalanges portion, and an ankle of the foot of the user. In one embodiment, the four flat-solid plates of the right sole and the left sole of the apparatus include a formed-tarsus plate, a metatarsal plate, a phalanges plate, and an ankle moving base plate. In one embodiment, the soles of the apparatus are the right and the left foot soles, respectively.

In one embodiment, the formed-tarsus plate of the right sole comprises a pair of studs. In one embodiment, a superior end of the formed-tarsus plate is hingedly and pivotally connected to an inferior end of the metatarsal plate of the right sole using, but not limited to, hinges. In one embodiment, the formed-tarsus plate of the right sole is connected to the connector by connecting the stud into the hole of the connector. In one embodiment, the superior end of the metatarsal plate is hingedly and pivotally connected to an inferior end of the phalanges plate of the right sole using, but not limited to, pivoting means.

In one embodiment, the formed-tarsus plate of the left sole comprises a pair of studs. In one embodiment, a superior end of the formed-tarsus plate is hingedly and pivotally connected to an inferior end of the metatarsal plate of the left sole using, but not limited to, hinges. In one embodiment, the superior end of the metatarsal plate is hingedly and pivotally connected to an inferior end of the phalanges plate of the left sole using, but not limited to, pivoting means. In another embodiment, the formed-tarsus plate, a metatarsal plate, a phalanges plate, and an ankle moving base plate of the right sole and left sole are connected by sandwiching between at least two layers of any soft and flexible materials, thereby providing flexibility in different directions for the user.

In one embodiment, the ankle moving base plate of the right sole comprises a loop, hinges, and a pair of holes. In one embodiment, an elongated rod is securely and pivotally connected to the ankle moving base plate of the right sole via the hinges using a hand-removable pin. In one embodiment, one end of the elongated rod is inserted into the hole of the right arm and another end of the elongated rod is slightly bended or bent for preventing an ankle moving strap or an ankle support strap from sliding off the right sole of the apparatus. In one embodiment, the ankle moving base plate of the left sole comprises a loop, hinges, and a pair of holes. In one embodiment, an elongated rod is securely and pivotally connected to the ankle moving base plate of the left sole via the hinges using a hand-removable pin. In one embodiment, one end of the elongated rod is inserted into the hole of the left arm and another end of the elongated rod is slightly bended or bent for preventing an ankle moving strap or an ankle support strap from sliding off the left sole of the apparatus.

In one embodiment, the right arm comprises at least two holes and the left arm comprises at least two holes. In one embodiment, the connector comprises a pair of holes and a U-shaped structure having a cut or an opening. In one embodiment, the right arm and the left arm are rotatably and adjustably connected to the connector via the holes and the cut of the connector using a knob and a pin-screw. The pin-screw is inserted into the holes of the right arm and the left arm, respectively and into the cut, thereby rotatably connecting the right arm and the left arm by tightening the knob to the pin-screw from another side. The right arm and the left arm are pivotally rotated independently around the centerline of the pin-screw and it could freely slide up and down in the cut.

In one embodiment, the apparatus further comprises a pair of ankle supports or a right-side ankle support and a left-side ankle support. The pair of ankle supports are securely and adjustably affixed to the right sole and the left sole of the apparatus. The right-side ankle support and the left-side ankle support are configured to support the ankle and lower leg of the foot of the user. In one embodiment, the right-side ankle support and the left-side ankle support comprise a soft pad with a plurality of straps. The soft pad is configured to relieve foot pressure and provide comfort for the user while using. The right-side ankle support further comprises a soft mean for covering the lateral side of the ankle and the inferior side of the lower leg of the user. The right-side ankle support further comprises a space for the heel to be freed. The plurality of straps includes a phalanges support strap with a loop and a soft but stiff mean. The soft but stiff mean is configured to align the toes of the foot of the user. The plurality of straps further includes a metatarsal strap with a loop and at least one ankle moving strap with a loop. In one embodiment, the plurality of straps of the right-side ankle support is configured to secure the right sole to the foot and the lower leg while lifting and lowering the foot of the user. In one embodiment, the plurality of straps could be, but not limited to, VELCRO® hook and loop material straps. The right sole and the left sole of the apparatus is securely and adjustably affixed to the pair of ankle supports, thereby allowing the user to flexibly adjust and secure feet on each sole of the apparatus. In one embodiment, the left-side ankle support comprises similar components of the right-side ankle support.

In one embodiment, the right sole and the left sole further comprises a right means and a left means. In one embodiment, the right shoe and the left shoe of the apparatus could be worn when the left means and the right means are in an inactive position. In another embodiment, the right shoe and the left shoe of the apparatus could be worn when the left means and the right means are in an active position. In one embodiment, the right shoe and the left shoe of the apparatus could be worn on both immobilized limbs and turned outward for enhancing treatment for the limb contractures. In another embodiment, the right shoe and the left shoe of the apparatus could be worn on both immobilized limbs of the user independently. In yet another embodiment, the right shoe and the left shoe of the apparatus could be worn on both immobilized limbs even they are connected via the connector without the use of the elongated rods.

In one embodiment, the right sole of the right shoe and the left sole of the left shoe of the apparatus could be worn on both immobilized limbs and independently turned in any direction for enhancing treatment for the limb contractures. In one embodiment, the plurality of straps of the right-side ankle support and the left-side ankle support are configured to secure the right sole and the left sole to the feet and lower leg of the user while lifting and lowering the foot using one or more additional straps that are coupled in one or more combinations to one or more loops of at least four-flat solid plates of the right sole, the left sole, the right arm, and the left arm by pulling, turning, and stretching the cartilages, tendons, and muscles of the user's feet, thereby treating limb contractures by manually lifting and lowering the feet of the user using the right shoe and the left shoe of the apparatus.

In another embodiment, the feet of the user could be automatically lifted and lowered using a lifting device and one or more additional straps.

One aspect of the present disclosure is directed to an apparatus for treating lower limb contractures, comprising (a) a pair of multi-sectional soles movably affixed to a connector via a pair of arms using fasteners, wherein the pair of soles configured to support a bottom of the feet of a user, wherein each multi-sectional sole of the apparatus, comprising: (i) at least four flat-solid plates securely and pivotally connected together via hinges and fasteners, wherein the four flat-solid plates are configured to cover, support, and align a tarsus portion, a metatarsal portion, a phalanges portion, and an ankle of the foot of the user, (b) a pair of ankle supports securely and adjustably affixed to each sole, configured to support the ankle and lower leg of the foot, wherein each ankle support, comprising: (i) a soft pad with a plurality of straps, wherein the soft pad is configured to relieve foot pressure and provide comfort for the user, wherein the plurality of straps is configured to secure the sole to the foot and lower leg of the user while lifting and lowering the user's feet using one or more additional straps that are coupled in one or more combinations to one or more loops of at least four-flat solid plates of the sole, thereby treating limb contractures by repetitive manually lifting and lowering the foot of the user using the apparatus.

In one embodiment, each multi-sectional sole of the apparatus is securely and adjustably affixed to each ankle support, thereby allowing the user to flexibly adjust and secure feet on each sole of the apparatus. In another embodiment, at least four flat-solid plates of each sole of the apparatus include a formed-tarsus plate, a phalanges plate, a metatarsal plate, and an ankle moving base plate. In a related embodiment, the tarsus plates of each sole are hingedly and pivotally connected to each metatarsal plate using one or more hinges, wherein the tarsus plates of each sole are further removably connected to a connector using studs via holes. In one embodiment, the phalange plates of each sole are hingedly and pivotally connected to each metatarsal plate via one or more pivoting means. In another embodiment, the ankle moving base plates of each sole are hingedly and pivotally connected to the pair of arms using an elongated rod and a hand-removable pin, wherein each arm is rotatably and adjustably connected to the connector via an opening using a rotatable nob and a fastener. In a related embodiment, each elongated rod of one is configured to secure the pair of arms and another end of the elongated rod is slightly bended or bent for preventing at least one strap from sliding off the pair of soles of the apparatus.

In one embodiment, the plurality of straps of each ankle support is configured to adjustably and detachably fastened to the user's ankle and lower leg, thereon for securing the feet and ankles to the sole of the apparatus, wherein the plurality of straps is VELCRO® hook and loop material straps. In another embodiment, the apparatus is further configured to adjust and align the lower limb of the user using the apparatus without applying any external force, thereby simply treating lower limb contractures by manually repetitive lifting and lowering the foot of the user using the apparatus. In one embodiment, the one or more additional straps are coupled in one or more combinations to one or more loops of the pair of arms for lifting and lowering the user's feet, thereby treating the limb contractures by pulling, turning, and stretching the cartilages, tendons, and muscles of the user's feet.

Another aspect of the present disclosure is directed to an apparatus for treating or preventing lower limb contractures, comprising: (a) a pair of soles movably affixed to a connector via a pair of arms using fasteners, configured to support a bottom of the feet of a user, wherein each sole of the apparatus, comprising: (i) at least four flat-solid plates securely and pivotally connected together via hinges and fasteners; (ii) wherein the four flat-solid plates are configured to cover, support, and align a tarsus portion, a metatarsal portion, a phalanges portion, and an ankle of the foot of the user; (b) a pair of ankle supports securely and adjustably affixed to each sole, configured to support the ankle and lower leg of the foot, wherein each ankle support, comprising: (i) a soft pad with a plurality of straps, wherein the soft pad is configured to relieve foot pressure and provide comfort for the user, wherein the plurality of straps is configured to secure the sole to the foot and lower leg of the user while lifting and lowering the foot using a lifting device and one or more additional straps that are coupled to one or more loops of at least four-flat solid plates of the sole, thereby treating limb contractures by automatically lifting and lowering the foot of the user using the apparatus.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to an ankle-foot moving apparatus and more particularly relates to an apparatus for treating or preventing lower limb contractures and lack of mobility in the lower limbs of an individual.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
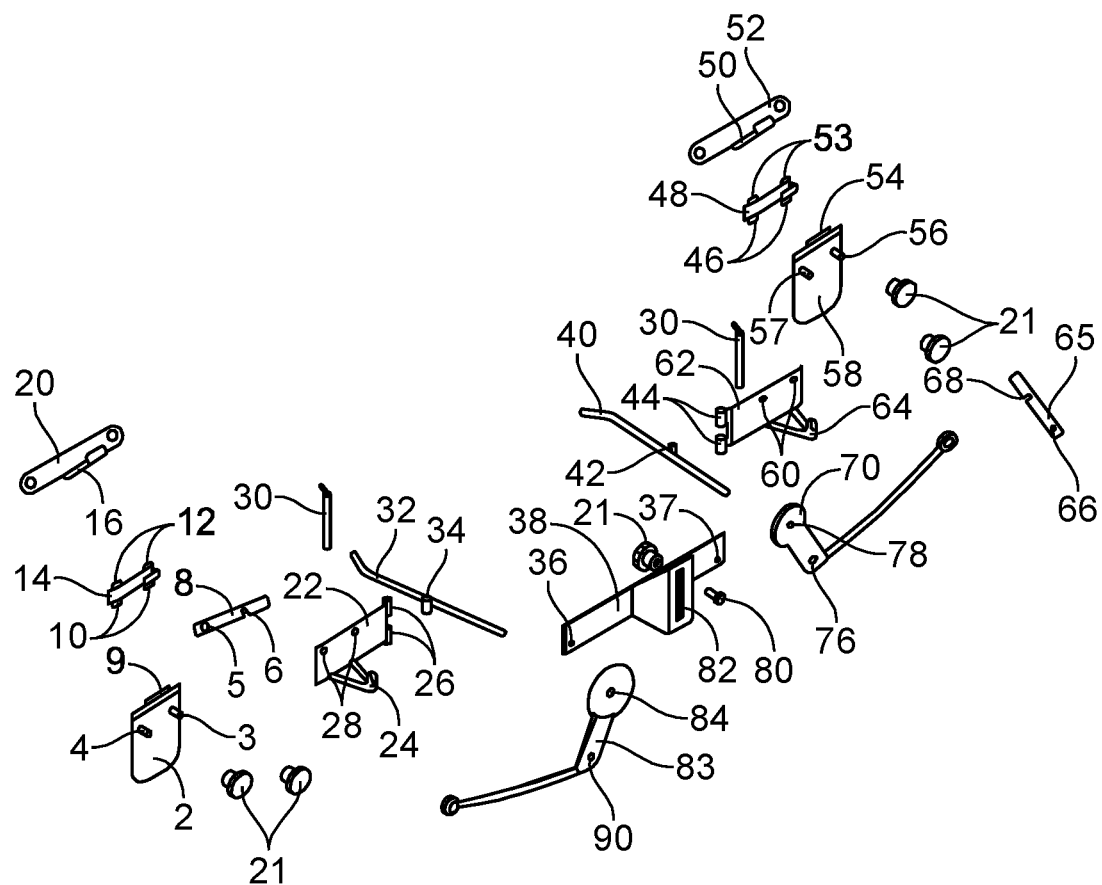
FIG. 1 illustrates an assembly of a pair of sole or a right sole and a left sole of an apparatus according to an embodiment of the present invention.

Referring to FIG. 1, an assembly of a pair of sole or a right sole 102 (shown in FIG. 7) and a left sole 103 (shown in FIG. 7) of an apparatus 101 is disclosed. In one embodiment, the apparatus 101 comprises a right shoe and a left shoe. In one embodiment, each sole (102 and 103) of the right shoe and the left shoe of the apparatus 101 is configured to support a bottom of the feet of a user. In one embodiment, the right sole 102 and the left sole 103 are movably affixed to a connector 38 via a pair of arms or a right arm and a left arm (83 and 70), respectively, using one or more fasteners.

In one embodiment, the right sole 102 and the left sole 103 of the apparatus 101 comprises at least four solid-plates, which are securely and pivotally connected via hinges and fasteners. The four flat-solid plates are configured to cover, support, and align a tarsus portion, a metatarsal portion, a phalanges portion, and an ankle of the foot of the user. In one embodiment, the four flat-solid plates of the right sole 102 and the left sole 103 of the apparatus 101 include a formed-tarsus plate (2 and 58), a metatarsal plate (14 and 48), a phalanges plate (20 and 52), and an ankle moving base plate (22 and 62). In one embodiment, the soles (102 and 103) of the apparatus 101 are the right and the left foot soles, respectively.

In one embodiment, the formed-tarsus plate 2 of the right sole 102 comprises a pair of studs (3 and 4). The pair of studs (3 and 4) are positioned at the posterior and approximate medial edge of the formed-tarsus plate 2. In one embodiment, a superior end of the formed-tarsus plate 2 is hingedly and pivotally connected to an inferior end of the metatarsal plate 14 of the right sole 102 using, but not limited to, hinges (9 and 10). In one embodiment, the formed-tarsus plate 2 of the right sole 102 is connected to the connector 38 by connecting the stud 3 into the hole 36 of the connector 38. In one embodiment, the superior end of the metatarsal plate 14 is hingedly and pivotally connected to an inferior end of the phalanges plate 20 of the right sole 102 using, but not limited to, pivoting means (12 and 16).

In one embodiment, the formed-tarsus plate 58 of the left sole 103 comprises a pair of studs (56 and 57). The pair of studs (56 and 57) are positioned at the posterior and approximate medial edge of the formed-tarsus plate 58. In one embodiment, a superior end of the formed-tarsus plate 58 is hingedly and pivotally connected to an inferior end of the metatarsal plate 48 of the left sole 103 using, but not limited to, hinges (46 and 54). In one embodiment, the formed-tarsus plate 58 of the left sole 103 is connected to the connector 38 by connecting the stud 57 into the hole 37 of the connector 38. In one embodiment, the superior end of the metatarsal plate 48 is hingedly and pivotally connected to an inferior end of the phalanges plate 52 of the left sole 103 using, but not limited to, pivoting means (50 and 53). In another embodiment, the formed-tarsus plate (2 and 58), a metatarsal plate (14 and 48), a phalanges plate (20 and 52), and an ankle moving base plate (22 and 62) of the right and left soles (102 and 103) are connected by sandwiching between at least two layers of fabric, thereby providing flexibility in different directions for the user.

In one embodiment, the ankle moving base plate 22 of the right sole 102 comprises a loop 24, hinges 26, and a pair of holes 28. The loop 24 is approximately positioned at an inferior end and the hinges 26 are positioned at the lateral side of the ankle moving base plate 22 of the right sole 102. The pair of holes 28 are approximately positioned at the superior end of the ankle moving base plate 22. In one embodiment, an elongated rod 32 is securely and pivotally connected to the ankle moving base plate 22 of the right sole 102 via the hinges (26 and 34) using a hand-removable pin 30. In one embodiment, one end of the elongated rod 32 is inserted into the hole 90 of the right arm 83 and another end of the elongated rod 32 is slightly bended or bent for preventing an ankle moving strap or an ankle support strap 122 from sliding off the right sole 102 of the apparatus 101.

In one embodiment, the ankle moving base plate 62 of the left sole 103 comprises a loop 64, hinges 44, and a pair of holes 60. The loop 64 is approximately positioned at an inferior end and the hinges 44 are positioned at the lateral side of the ankle moving base plate 62 of the left sole 103. The pair of holes 60 are approximately positioned at the superior end of the ankle moving base plate 62. In one embodiment, an elongated rod 40 is securely and pivotally connected to the ankle moving base plate 62 of the left sole 103 via the hinges (42 and 44) using a hand-removable pin 30. In one embodiment, one end of the elongated rod 40 is inserted into the hole 76 of the left arm 70 and another end of the elongated rod 40 is slightly bended or bent for preventing an ankle moving strap or an ankle support strap 122 from sliding off the left sole 103 of the apparatus 101.

In one embodiment, a right means 8 is rotatably connected to at least one stud 4 of the formed-tarsus plate 2 of the right sole 102 via a hole 5. The right means 8 includes a cut or an arched portion 6. In one embodiment, a left means 65 is rotatably connected to at least one stud 56 of the formed-tarsus plate 58 of the left sole 103 via a hole 66. The left means 65 includes a cut or an arched portion 68.

In one embodiment, the right arm 83 comprises at least two holes (84 and 90) and the left arm 70 comprises at least two holes (76 and 78). In one embodiment, the connector 38 comprises a pair of holes (36 and 37) and a U-shaped structure having a cut or an opening 82. The pair of holes (36 and 37) are approximately positioned on lateral sides of the connector 38. The cut or opening 82 of the U-shaped structure is positioned at a posterior and medial side. In one embodiment, the right arm 83 and the left arm 70 are rotatably and adjustably connected to the connector 38 via the holes (84 and 78) and the cut 82 of the connector 38 using a knob 21 and a pin-screw 80.

The pin-screw 80 is inserted into the holes (84 and 78) of the right arm 83 and the left arm 70, respectively and into the cut 82, thereby rotatably connecting the right arm 83 and the left arm 70 by tightening the knob 21 to the pin-screw 80 from another side. The right arm 83 and the left arm 70 are pivotally rotated independently around the centerline of the pin-screw 80 and it could freely slide up and down in the cut 82.

Figure 2:
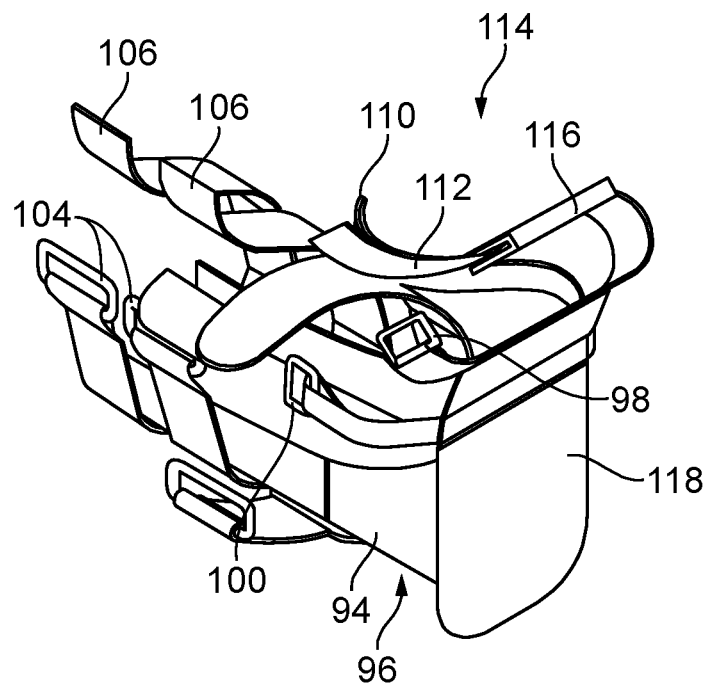
FIG. 2 shows a perspective view of a right-side ankle support of the apparatus according to one embodiment of the present invention.

Referring to FIG. 2, a right-side ankle support 114 of the apparatus 101 is disclosed. In one embodiment, the apparatus 101 further comprises a pair of ankle supports or a right-side ankle support 114 and a left-side ankle support 105 (shown in FIG. 3). The pair of ankle supports (114 and 105) are securely and adjustably affixed to the right sole 102 (shown in FIG. 7) and the left sole 103 (shown in FIG. 7) of the apparatus 101. The right-side ankle support 114 is configured to support the ankle and lower leg of the foot of the user. In one embodiment, the right-side ankle support 114 and the left-side ankle support 105 comprise a soft pad 118 with a plurality of straps. The soft pad 118 is configured to relieve foot pressure and provide comfort for the user while using.

The right-side ankle support 114 further comprises a soft mean 94 for covering the lateral side of the ankle and the inferior side of the lower leg of the user. The right-side ankle support 114 further comprises a space 96 for the heel to be freed. The plurality of straps includes a phalanges support strap 112 with a loop 98 and a soft but stiff mean 116. The soft but stiff mean 116 is configured to align the toes of the foot of the user. The plurality of straps further includes a metatarsal strap 110 with a loop 100 and at least one ankle strap 106 with a loop 104. In one embodiment, the plurality of straps of the right-side ankle support 114 is configured to secure the right sole 102 to the foot and the lower leg while lifting and lowering the foot of the user. In one embodiment, the plurality of straps could be, but not limited to, VELCRO® hook and loop material straps. The right sole 102 and the left sole 103 of the apparatus 101 is securely and adjustably affixed to the pair of ankle supports, thereby allowing the user to flexibly adjust and secure feet on each sole (102 and 103) of the apparatus 101. In one embodiment, the left-side ankle support 105 comprises similar components of the right-side ankle support 114.

Figure 3:
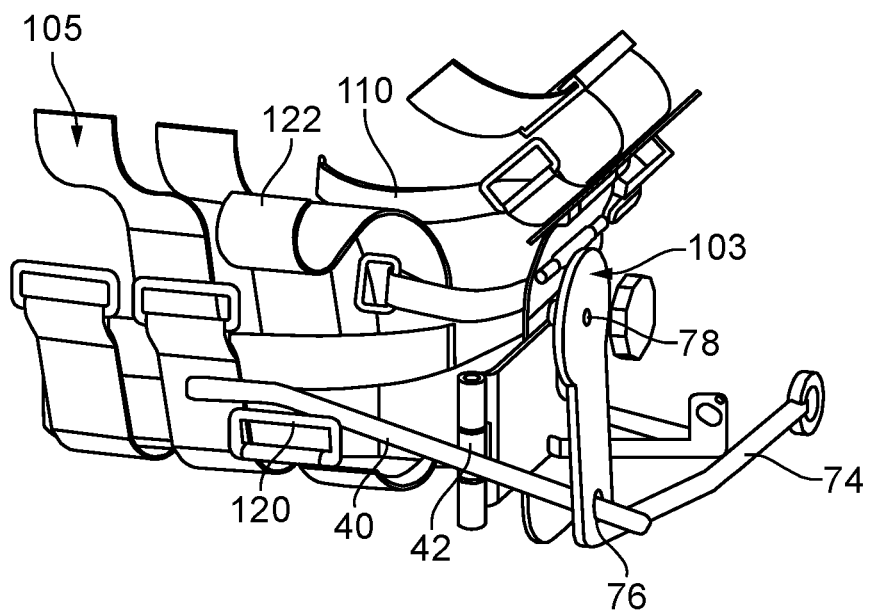
FIG. 3 shows a perspective view of a left-side ankle support is connected to the left sole of the apparatus according to one embodiment of the present invention.

Referring to FIG. 3, the left-side ankle support 105 is connected to the left sole 103 of the apparatus 101 is disclosed. In one embodiment, the left-side ankle support 105 is adjustably and flexibly connected to the left sole 103 of the apparatus. In one embodiment, the left-side ankle support 105 further comprises an ankle moving strap 122 with a loop 120. In one embodiment, the ankle moving strap 122 could be, but not limited to, a VELCRO® hook and loop material strap. In one embodiment, the elongated rod 40 is configured to prevent the ankle moving strap 122 from sliding off the left sole 103 of the apparatus 101.

Figure 4:
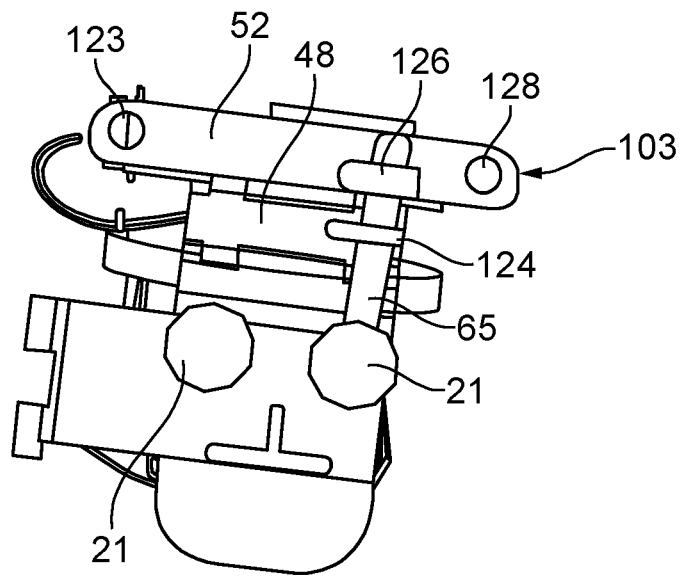
FIG. 4 illustrates a bottom perspective view of the left sole of the apparatus according to one embodiment of the present invention.

Referring to FIG. 4, the left sole 103 of the apparatus 101 is disclosed. The left sole 103 of the apparatus 101 comprises a phalanges plate 52. In one embodiment, the phalanges plate 52 of the left shoe of the apparatus 101 comprises a pair of loops or holes (123 and 128). The pair of loops or holes (123 and 128) are positioned at the lateral sides of the phalanges plate 52. In one embodiment, the phalanges plate 52 of the left shoe of the apparatus 101 further comprises a half-bridge 126. In one embodiment, the metatarsal plate 48 of the left shoe of the apparatus 101 comprises a half-bridge 124. In one embodiment, the formed-tarsus plate 58, the metatarsal plate 48, and the phalanges plate 52 are configured to align and adjust into a one-piece solid body by positioning the left means 65 in the active state and by tightening the knob 21.

Figure 5:
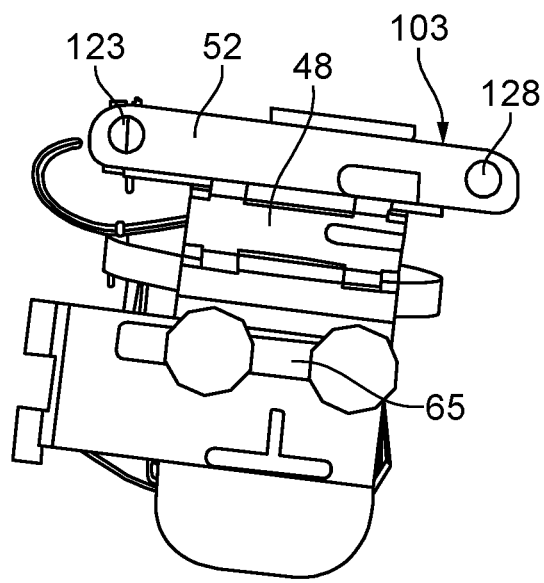
FIG. 5 shows a bottom perspective view of the left sole of the apparatus in a flexible state according to one embodiment of the present invention.

Referring to FIG. 5, the left sole of the apparatus in a flexible state is disclosed. In one embodiment, the left means 65 is in an inactive position or a flexible state. In one embodiment, the formed-tarsus plate 58, the metatarsal plate 48, and the phalanges plate 52 are freed or flexible when the left means 65 is in the inactive position, thereby easily accepting the foot with a shape in a contracture state by the left sole 103 of the left shoe of the apparatus 101. In one embodiment, the right shoe and the left shoe of the apparatus 101 could be worn when the left means 65 and the right means 8 are in an inactive position. In another embodiment, the right shoe and the left shoe of the apparatus 101 could be worn when the left means 65 and the right means 8 are in an active position.

Figure 6:
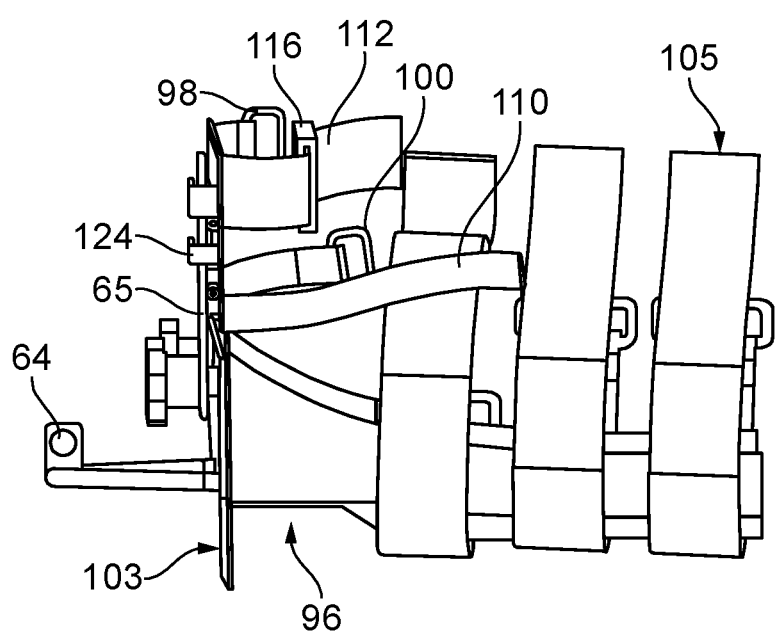
FIG. 6 shows a side perspective view of the left sole of the apparatus in an active position according to one embodiment of the present invention.

Referring to FIG. 6, the left sole 103 of the apparatus 101 in an active position is disclosed. In one embodiment, the left means 65 of the left sole 103 includes a cut or an arched portion 68. When the left means 65 is in the active position, the cut or the arched portion 68 of the left means 65 is connected to the half-bridge 124 of the metatarsal plate 48 of the left shoe of the apparatus 101, thereby aligning the formed-tarsus plate 58, the metatarsal plate 48, and the phalanges plate 52 corresponding to the shape of the foot of the user. The space 96 of the left-side ankle support 105 could be adjusted corresponding to the position of the heel and the ankle of the user, thereby freely moving the heel and the ankle of the user within the space 96. In one embodiment, the ankle moving base plate 62 of the left sole 103 comprises a loop 64.

Figure 7:
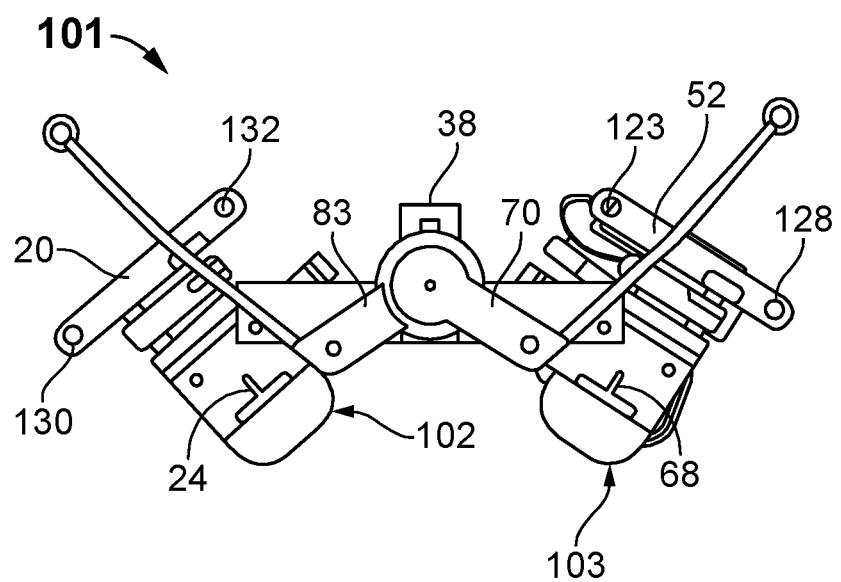
FIG. 7 shows a bottom perspective view of the right sole and the left sole of the apparatus turned outward for enhancing treatment for limb contractures according to one embodiment of the present invention.

Referring to FIG. 7, the right sole 102 and the left sole 103 of the apparatus 101 are turned outward for enhancing treatment for limb contractures is disclosed. In one embodiment, the right sole 102 and the left sole 103 are movably connected to the connector 38 using the right arm 83 and the left arm 70. The right shoe and the left shoe of the apparatus 101 could be worn on both immobilized limbs and turned outward for enhancing treatment for the limb contractures. In another embodiment, the right shoe and the left shoe of the apparatus 101 could be worn on both immobilized limbs of the user independently. In yet another embodiment, the right shoe and the left shoe of the apparatus 101 could be worn on both immobilized limbs even they are connected via the connector 38 without the use of the elongated rods (32 and 40). In one embodiment, the phalanges plates (20 and 52) of the right shoe and the left shoe of the apparatus 101 comprises a pair of loops or holes (123 and 128) (130 and 132), respectively.

Figure 8:
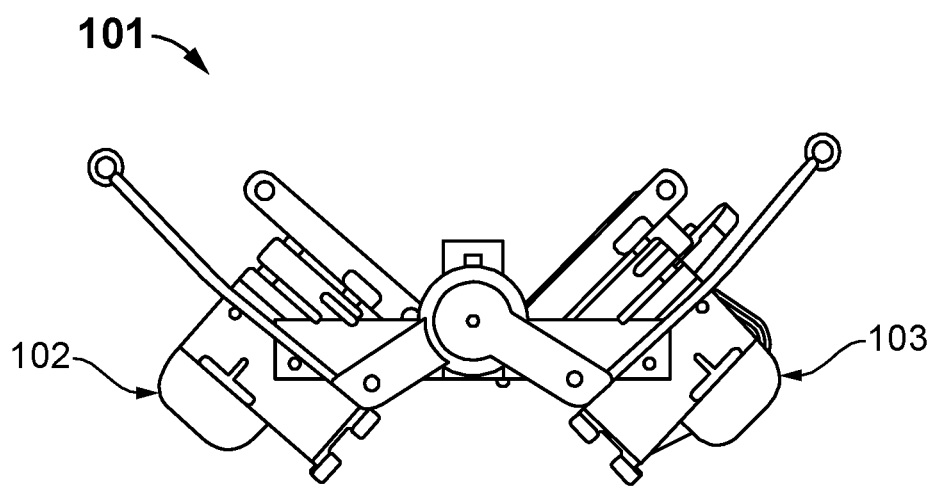
FIG. 8 shows a bottom perspective view of the right sole and the left sole of the apparatus turned inward for enhancing treatment for limb contractures according to one embodiment of the present invention.

Referring to FIG. 8, the right sole 102 and the left sole 103 of the apparatus 101 are turned inward for enhancing treatment for limb contractures is disclosed. The right sole 102 of the right shoe and the left sole 103 of the left shoe of the apparatus 101 could be worn on both immobilized limbs and independently turned inward for enhancing treatment for the limb contractures.

Figure 9:
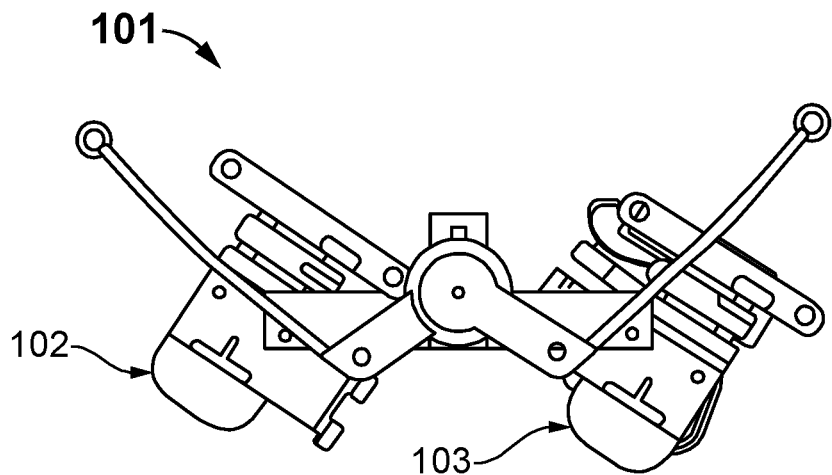
FIG. 9 shows a bottom perspective view of the right sole turned inward and the left sole of the apparatus turned outward for enhancing treatment for limb contractures according to one embodiment of the present invention.

Referring to FIG. 9, the right sole 102 and the left sole 103 of the apparatus 101 are turned or moved in a direction for enhancing treatment for limb contractures is disclosed. The right sole 102 and the left sole 103 of the apparatus 101 could be worn on both immobilized limbs and the right sole 102 of the right shoe is turned inward direction and the left sole 103 of the left shoe of the apparatus 101 turned in the outward direction for enhancing treatment for the limb contractures.

Figure 10:
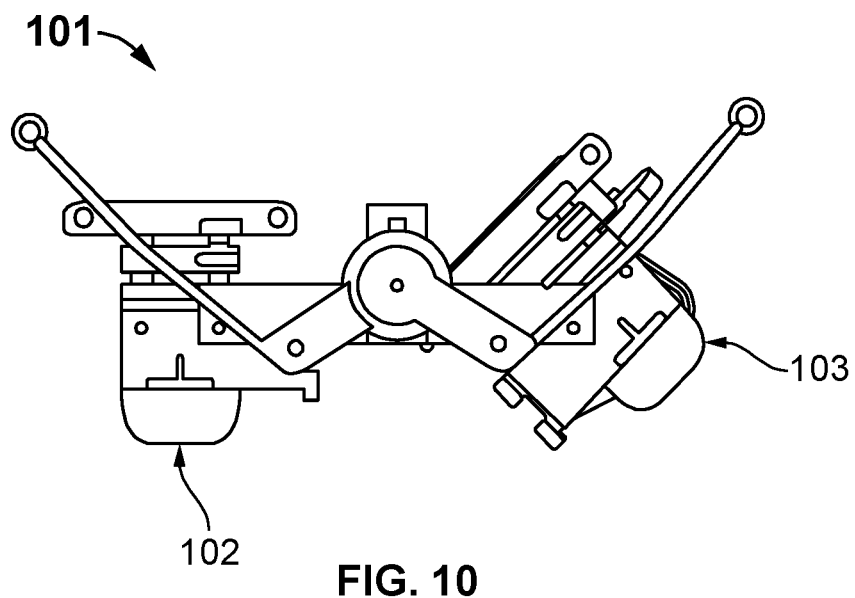
FIG. 10 shows a bottom perspective view of the right sole kept straight and the left sole of the apparatus turned inward for enhancing treatment for limb contractures according to one embodiment of the present invention.

Referring to FIG. 10, the right sole 102 and the left sole 103 of the apparatus 101 are turned or moved in a direction for enhancing treatment for limb contractures is disclosed. The right sole 102 and the left sole 103 of the apparatus 101 could be worn on both immobilized limbs and the right sole 102 of the right shoe is kept in straight and the left sole 103 of the left shoe is turned in the inward direction for enhancing treatment for the limb contractures.

Figure 11:
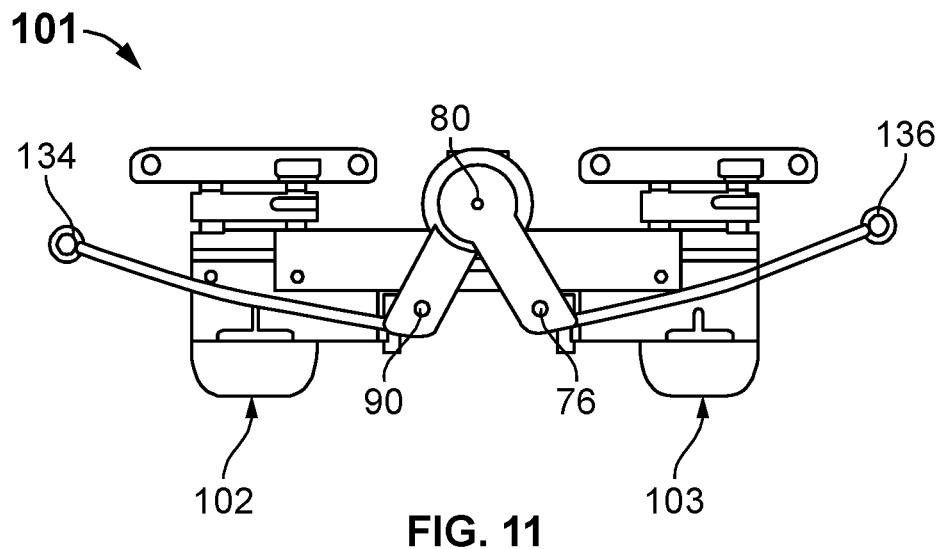
FIG. 11 shows a bottom perspective view of the right sole and the left sole of the apparatus with loops and a right arm and a left arm of the apparatus are in a relaxed state according to one embodiment of the present invention.
Figure 12:
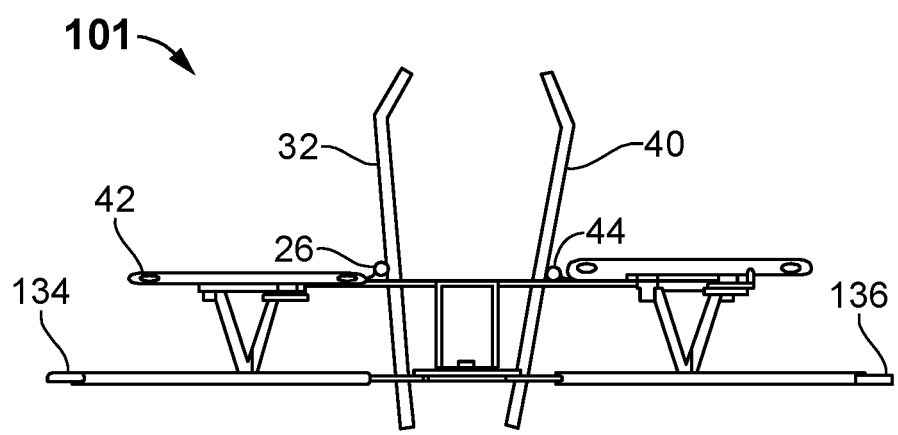
FIG. 12 shows a top view of the right sole and the left sole of the apparatus with loops and a right arm and a left arm of the apparatus are in the relaxed state according to one embodiment of the present invention.

Referring to FIGS. 11-12, the right arm 83 and the left arm 70 of the apparatus 101 are in a relaxed state is disclosed. In one embodiment, the right arm 83 and the left arm 70 further comprising at least one loop (134 and 136) and at least one hole (90 and 76), respectively. The holes (90 and 76) are configured to receive the elongated rods (32 and 40), respectively and are at closest distance from each other when the right arm 83 and the left arm 70 are in the relaxed state. In this state, the pin-screw 80 is in the highest position in the cut 82 (shown in FIG. 1) of the connector 38. In one embodiment, the elongated rods (32 and 40) are connected to the ankle moving base (22 and 62) using hinges (26 and 44).

Figure 13:
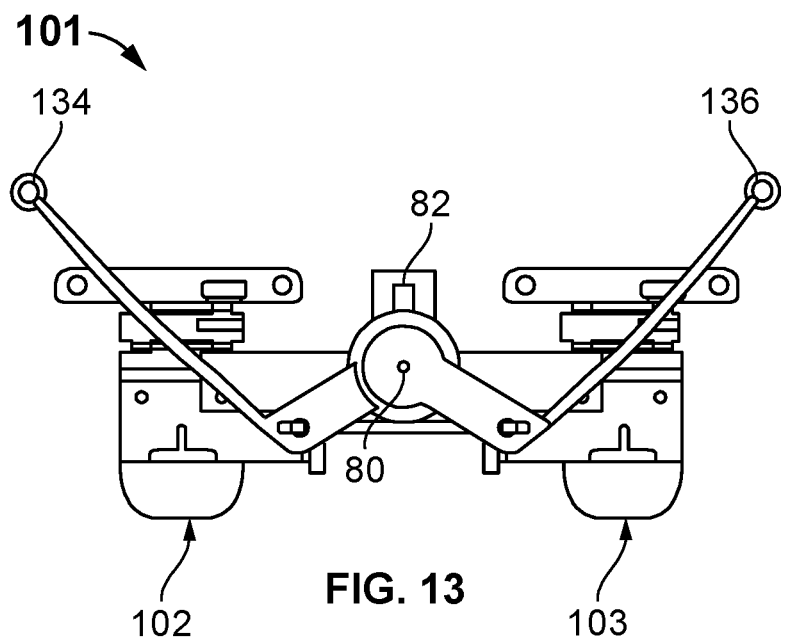
FIG. 13 shows a bottom view of the right sole and the left sole of the apparatus with loops and a right arm and a left arm of the apparatus are in a pulled-up state according to one embodiment of the present invention.
Figure 14:
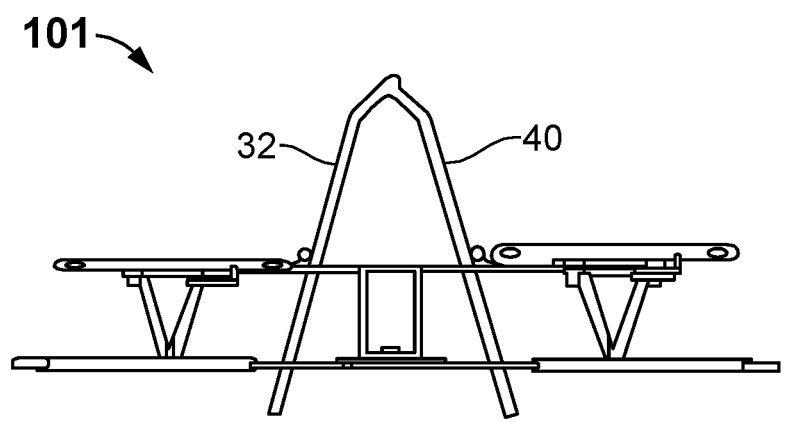
FIG. 14 shows a top view of the right sole and the left sole of the apparatus with loops and a right arm and a left arm of the apparatus are in the pulled-up state according to one embodiment of the present invention.

Referring to FIGS. 13-14, the right arm 83 and the left arm 70 of the apparatus 101 are in a pulled-up state is disclosed. In one embodiment, the elongated rods (32 and 40) are at the farthest distance from each other when the right arm 83 and the left arm 70 are in the pulled-up state. In this state, the pin-screw 80 is in the lowest position in the cut 82 of the connector 38. In one embodiment, one end of the elongated rods (32 and 40) are inserted into the holes (90 and 76) of the right arm 83 and the left arm 70 and another end of the elongated rod (32 and 40) are slightly bended or bent for preventing an ankle moving strap or an ankle support strap 122 from sliding off the left sole 103 of the apparatus 101 and another ends of the elongated rods (32 and 40) are closest to each other when the right arm 83 and the left arm 70 are in the pulled-up state.

In one embodiment, the elongated rods (32 and 40) are securely and pivotally connected to the ankle moving base plates (22 and 62) of the right sole 102 and the left sole 103 via the hinges (26 and 34) (44 and 42), respectively, using hand-removable pins 30. In one embodiment, the ankle support straps 122 are fastened around the ankle on the right foot and the left foot of the user.

In one embodiment, the plurality of straps of the right-side ankle support 114 (shown in FIG. 2) and the left-side ankle support 105 are configured to secure the right sole 102 and the left sole 103 to the feet and lower leg of the user while lifting and lowering the foot using one or more additional straps that are coupled in one or more combinations to one or more loops (123, 128, 130, 132, 24, 64, 134 and 136) of at least four-flat solid plates of the right sole 102, the left sole 103, the right arm 83, and the left arm 70, thereby treating limb contractures by manually repetitive lifting and lowering the feet of the user using the right shoe and the left shoe of the apparatus 101.

Figure 15:
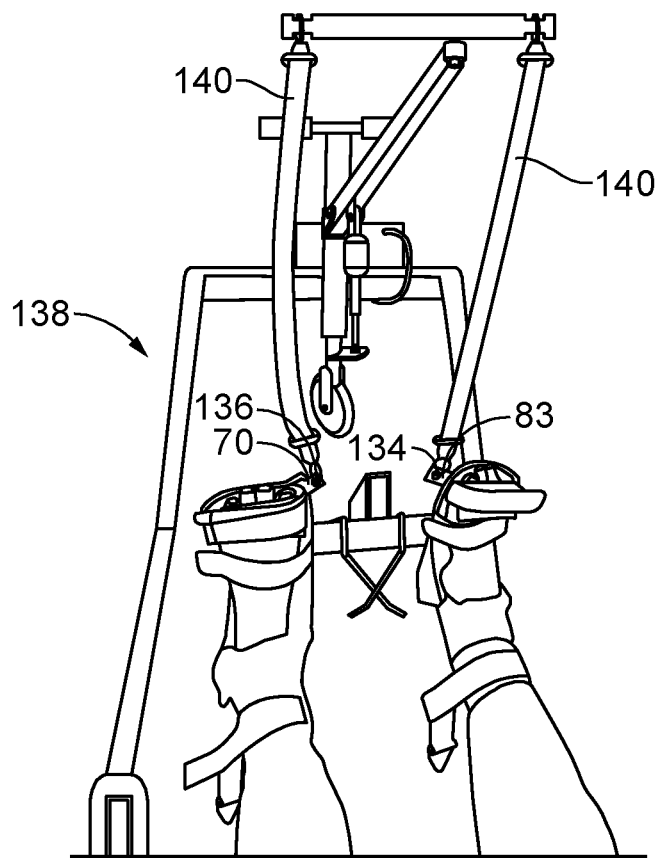
FIG. 15 shows a perspective view of a lifting device used to lift and lower the user feet using one or more additional straps for treating lower limb contractures according to one embodiment of the present invention.

Referring to FIG. 15, the lifting device 138 used to lift and lower the user feet using a pair of additional straps 140 for treating lower limb contractures is disclosed. In another embodiment, the feet of the user could be automatically lifted and lowered using the lifting device 138 and the additional straps 140. In one embodiment, the additional straps 140 are securely connected to both loops (134 and 136) of the right arm 83 and the left arm 70 and upon lifting and lowering the additional straps 140 using the lifting device 138 and repeating the lifting and lowering the additional straps 140 for several times, thereby treating and mobilizing the lower limb contractures by pulling, turning, and stretching the cartilages, tendons, and muscles of the user's feet. In one embodiment, the force of gravity will be affected on the limbs of the user during the process of treatment. In one embodiment, an external force could be applied for pulling, pushing, turning, and stretching the shortened muscle as a result of the weight of the limb and by repeating the action for the proper elevation and timing, the main cause of contracture is eliminated.

In one embodiment, an additional strap 140 is reversibly coupled to the loop 123 of the phalanges plate 52 (shown in FIG. 7) and upon lifting and releasing the strap for several times by manually or using a lifting device 138, thereby treating and mobilizing lower limb contractures by turning the cartilages, tendons, and muscles of the foot of the user while the other foot is in an immobilized position.

In one embodiment, an additional strap 140 is reversibly coupled to the loop 128 of the phalanges plate 52 and upon lifting and releasing the additional strap 140 for several times by manually or using a lifting device 138, thereby treating and mobilizing lower limb contractures by turning the cartilages, tendons, and muscles of the foot of the user.

In another embodiment, one or more additional straps 140 are reversibly coupled to the loops (123 and 128) of the phalanges plate 52 and upon lifting and releasing the additional straps 140 for several times by manually or using a lifting device 138, thereby treating and mobilizing lower limb contractures by turning the cartilages, tendons, and muscles of the foot of the user while the other foot is in the immobilized position.

In yet another embodiment, an additional strap 140 is reversibly coupled to the loop 130 of the phalanges plate 20 and upon lifting and releasing the additional strap 140 for several times by manually or using a lifting device 138, thereby treating and mobilizing lower limb contractures by turning and stretching the cartilages, tendons, and muscles of the foot of the user while the other foot is in the immobilized position.

In yet another embodiment, an additional strap 140 is reversibly coupled to the loop 132 of the phalanges plate 20 and upon lifting and releasing the additional strap 140 for several times by manually or using a lifting device 138, thereby treating and mobilizing lower limb contractures by turning and stretching the cartilages, tendons, and muscles of the foot of the user.

In yet another embodiment, one or more additional straps/a pair of additional straps 140 are reversibly coupled to the loops (130 and 132) of the phalanges plate 20 and upon lifting and releasing the additional straps 140 for several times by manually or using a lifting device 138, thereby treating and mobilizing lower limb contractures by pulling and stretching the cartilages, tendons, and muscles of the foot of the user.

In yet another embodiment, an additional strap 140 is reversibly coupled to the loop 24 of the ankle moving base plate 22 and upon lifting and releasing the additional strap 140 for several times by manually or using a lifting device 138, thereby treating and mobilizing lower limb contractures by turning and stretching the cartilages, tendons, and muscles of the foot of the user while the other foot is in an immobilized position.

In yet another embodiment, an additional strap 140 is reversibly coupled to the loop 64 of the ankle moving base plate 62 and upon lifting and releasing the additional strap 140 for several times by manually or using a lifting device 138, thereby treating and mobilizing lower limb contractures by turning and stretching the cartilages, tendons, and muscles of the foot of the user while the other foot is in an immobilized position.

In yet another embodiment, one or more additional straps/a pair of additional straps 140 are reversibly coupled to the loops (24 and 64) of both ankle moving base plates (22 and 62) and upon lifting and releasing the additional straps 140 for several times by manually or using a lifting device 138, thereby treating and mobilizing lower limb contractures by turning, pulling, and stretching the cartilages, tendons, and muscles of the feet of the user.

In yet another embodiment, a pair of additional or more additional straps 140 are reversibly coupled to one or more combinations of loops (123, 128, 130, and 132) of both phalanges plates (20 and 52) and upon lifting and releasing the additional straps 140 for several times by manually or using a lifting device 138, thereby treating and mobilizing lower limb contractures by pulling, turning, and stretching the cartilages, tendons, and muscles of the feet of the user.

In yet another embodiment, a pair of additional straps 140 are reversibly coupled to the loops (24 and 64) of the ankle moving base plates (22 and 62) when the user's feet turned in any desired angle and upon lifting and releasing the additional straps 140 for several times by manually or using a lifting device 138, thereby treating and mobilizing lower limb contractures by pulling, turning, and stretching the cartilages, tendons, and muscles of the user's feet.

In yet another embodiment, a pair of or more additional straps 140 are reversibly coupled to the loops (123, 128, 130, and 132) of both phalanges plates (20 and 52) while the nobs of studs (3 and 57) of the formed-tarsus plate (2 and 58) are loose and upon lifting and releasing the additional straps 140 for several times by manually or using a lifting device 138, thereby treating and mobilizing lower limb contractures by pulling, turning, and stretching the cartilages, tendons, and muscles of the user's feet.

In yet another embodiment, at least one additional strap or a pair of additional straps 140 are reversibly coupled to loop (24 and 64) of the ankle moving base plate (22 and 62) when the left foot and the right foot are turned outward (shown in FIG. 7) while the nobs of studs (3 and 57) of the formed-tarsus plate (2 and 58) are tightened and upon lifting and releasing the additional straps 140 for several times by manually or using a lifting device 138, thereby treating and mobilizing lower limb contractures by pulling, turning, and stretching the cartilages, tendons, and muscles of the user's feet.

In yet another embodiment, the one or more additional straps 140 are reversibly coupled in one or more combinations to one or more loops (123, 128, 130, 132, 24, 64, 134 and 136) of at least four-flat solid plates of the right sole 102, the left sole 103, the right arm 83, and the left arm 70, thereby treating and mobilizing the limb contractures by manually repetitive lifting, lowering, pulling, turning, and stretching the cartilages, tendons, and muscles of the user's feet for several times using the additional straps 140 by manually or using a lifting device 138.

In yet another embodiment, the one or more additional straps 140 are reversibly coupled in one or more combinations to one or more loops (123, 128, 130, 132, 24, 64, 134 and 136) of at least four-flat solid plates of the right sole 102, the left sole 103, the right arm 83, and the left arm 70, thereby treating and mobilizing the limb contractures by manually lifting, lowering, pulling, turning, and stretching the cartilages, tendons, and muscles of the user's feet for several times using the additional straps 140 by manually or using a lifting device 138.

In yet another embodiment, the one or more additional straps 140 are reversibly coupled in one or more combinations to one or more loops (123, 128, 130, 132, 24, 64, 134 and 136) of at least four-flat solid plates of the right sole 102, the left sole 103, the right arm 83, and the left arm 70, when the left foot and the right foot are turned in any direction while the nobs of studs (3 and 57) of the formed-tarsus plate (2 and 58) are tightened or loosened and upon lifting and releasing the additional straps 140 for several times by manually or using a lifting device 138, thereby treating and mobilizing lower limb contractures by pulling, turning, and stretching the cartilages, tendons, and muscles of the user's feet.

In yet another embodiment, when a pair of additional straps 140 are reversibly coupled to loops (134 and 136) of the right arm 83 and the left arm 70 and upon lifting and lowering the additional straps 140 by manually or using a lifting device 138, the ankles move inward and outward, respectively, by fastening the ankle moving straps 122 to the elongated rods (32 and 40) and repeating the lifting and lowering the straps for several times, thereby treating and mobilizing the lower limb contractures by pulling, turning, and stretching the cartilages, tendons, and muscles of the user's feet. In one embodiment, the force of gravity will be affected on the limbs of the user during the process of treatment. In one embodiment, an external force could be applied for pulling, pushing, turning, and stretching the shortened muscle as a result of the weight of the limb and by repeating the action for the proper elevation and timing, the main cause of contracture may be eliminated.

The advantages of the present invention include: the apparatus 101 could approach for attending to the consequences of prolonging immobility and more particularly contracture. The apparatus 101 could enable the organs include the cartilages, tendons, muscles, and blood vessels to mobilize even passively and remain healthy. The apparatus 101 is easy to use, safe, reliable, flexible, and provides comfort for the user while using. The apparatus 101 could be used and suitable for any person who is suffering from the lower limb contractures.

The foregoing description comprises illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions.

Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

The invention claimed is:

1. An apparatus for treating lower limb contractures, comprising:
 a pair of multi-sectional soles movably affixed to a connector via a pair of arms using fasteners,
 wherein the pair of multi-sectional soles configured to support a bottom of the feet of a user, wherein each sole of the apparatus, comprising:
  at least four flat-solid plates securely and pivotally connected together via hinges and fasteners,
  wherein the four flat-solid plates are configured to cover, support, and align a tarsus portion, a metatarsal portion, a phalanges portion, and an ankle of the foot of the user;
 a pair of ankle supports securely and adjustably affixed to each sole, configured to support the ankle and lower leg of the foot, wherein each ankle support, comprising:
  a soft pad with a plurality of straps, wherein the soft pad is configured to relieve foot pressure and provide comfort for the user, wherein the plurality of straps are configured to secure the sole of the foot and lower leg of the user while lifting and lowering at least one user's foot using one or more additional straps that are coupled in one or more combinations to one or more loops of the at least four-flat solid plates of the sole, thereby treating limb contractures by a means of lifting and lowering the foot of the user using the apparatus.

2. The apparatus of claim 1, wherein each multi-sectional sole of the apparatus is securely and adjustably affixed to each ankle support, thereby allowing the user to flexibly adjust and secure feet on each sole of the apparatus.

3. The apparatus of claim 1, wherein the at least four flat-solid plates of each sole of the apparatus include a formed-tarsus plate, a phalanges plate, a metatarsal plate, and an ankle moving base plate.

4. The apparatus of claim 3, wherein the tarsus plate of each sole are hingedly and pivotally connected to each metatarsal plate, which also comprise a half-bridge, using one or more hinges, wherein the tarsus plate of each sole are further removably connected to a connector using studs via holes.

5. The apparatus of claim 3, wherein the phalange plate, which also comprise a half-bridge, of each sole are hingedly and pivotally connected to each metatarsal plate via one or more pivoting means.

6. The apparatus of claim 3, wherein the ankle moving base plate of each sole are hingedly and pivotally connected to the pair of arms using an elongated rod and a hand-removable pin, wherein each arm is rotatably and adjustably connected to the connector via an opening using a rotatable knob and a fastener.

7. The apparatus of claim 6, wherein each elongated rod of one is configured to secure the pair of arms and another end of the elongated rod is slightly bended or bent for preventing at least one strap from sliding off the pair of soles of the apparatus.

8. The apparatus of claim 3, wherein the formed-tarsus plate, the metatarsal plate, and the phalanges plate are configured to align and adjust into a one-piece solid body by positioning a left means in an active state and by tightening a knob.

9. The apparatus of claim 3, wherein a right shoe and a left shoe of the apparatus can be worn when the lifting and lowering of at least one foot of the user is in an inactive position.

10. The apparatus of claim 3, wherein a right shoe and a left shoe of the apparatus can be worn when the lifting and lowering of at least one foot of the user is in an active position.

11. The apparatus of claim 1, wherein the plurality of straps of each ankle support is configured to be adjustably and detachably fastened to the user's ankle and lower leg, thereon for securing the feet and ankles to the sole of the apparatus, wherein the plurality of straps is VELCRO® hook and loop material straps.

12. The apparatus of claim 1, is further configured to adjust and align the lower limb of the user using the apparatus without applying any external force, thereby simply treating lower limb contractures by manually repetitive lifting and lowering the foot of the user using the apparatus.

13. The apparatus of claim 1, wherein the one or more additional straps are coupled in one or more combinations to one or more loops of the pair of arms for lifting and lowering the user's feet, thereby treating the limb contractures by pulling, turning, and stretching the cartilages, tendons, and muscles of the user's feet.

* * * * *